(12) United States Patent
Zheng et al.

(10) Patent No.: US 11,432,353 B2
(45) Date of Patent: *Aug. 30, 2022

(54) SYSTEMS, APPARATUSES AND METHODS FOR SECURE INDUCTIVE PAIRING BETWEEN TWO DEVICES

(71) Applicant: Becton, Dickinson and Company, Franklin Lakes, NJ (US)

(72) Inventors: Ping Zheng, Acton, MA (US); Marc Clifford Vogt, Rye, NH (US); Mojtaba Kashef, Boxford, MA (US); Sumukh Pathare, Dublin, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/329,575

(22) Filed: May 25, 2021

(65) Prior Publication Data

US 2021/0321470 A1 Oct. 14, 2021

Related U.S. Application Data

(63) Continuation of application No. 16/497,068, filed as application No. PCT/US2018/023299 on Mar. 20, 2018, now Pat. No. 11,039,491.

(Continued)

(51) Int. Cl.
*H04W 76/14* (2018.01)
*H04B 5/00* (2006.01)
*H04W 48/12* (2009.01)

(52) U.S. Cl.
CPC .......... *H04W 76/14* (2018.02); *H04B 5/0031* (2013.01); *H04B 5/0075* (2013.01); *H04W 48/12* (2013.01)

(58) Field of Classification Search
CPC .................................. H04W 4/80; H04B 5/00
See application file for complete search history.

(56) References Cited

U.S. PATENT DOCUMENTS 8,619,739 B1  12/2013  Donovan et al.
8,861,505 B1  10/2014  De la Broise et al.
(Continued)

OTHER PUBLICATIONS

International Search Report dated Jun. 14, 2018, which issued in corresponding PCT Patent Application No. PCT/US2018/023299.
(Continued)

*Primary Examiner* — Cindy Trandai
(74) *Attorney, Agent, or Firm* — Dickinson Wright PLLC

(57) ABSTRACT

Devices, systems and methods are provided to improve pairing between two devices by employing an inductive antenna circuit (e.g., 13.56 MHz) in addition to another wireless communication antenna circuit (e.g., 2.4 GHz) and a pairing protocol to minimize pairing between unintended devices. Communications via inductive antenna circuit (e.g., 13.56 MHz) require that the devices to be paired to be in close proximity to each other, which increases the likelihood of intended pairing between these devices. When the inductive pulses of the first device are detected by the second device, the second device commences advertising signals with time stamps. The inductive pulses and the time stamps facilitate synchronizing scanning windows of the first device with the advertising signals of the second device to lessen the likelihood of interference of advertising pulses from an unintended device.

6 Claims, 13 Drawing Sheets

Related U.S. Application Data

(60) Provisional application No. 62/478,256, filed on Mar. 29, 2017.

(56) References Cited

U.S. PATENT DOCUMENTS

| | | | |
|---|---|---|---|
| 9,396,368 | B1 | 7/2016 | Lamba |
| 10,170,917 | B1 | 1/2019 | Bell |
| 11,178,529 | B2* | 11/2021 | Chong .................. H04L 67/12 |
| 2002/0097182 | A1 | 7/2002 | Goren |
| 2003/0114897 | A1 | 6/2003 | Von Arx et al. |
| 2009/0070797 | A1 | 3/2009 | Ramaswamy |
| 2013/0143488 | A1 | 6/2013 | Royston et al. |
| 2014/0011446 | A1 | 1/2014 | Kangas et al. |
| 2014/0057564 | A1 | 2/2014 | Palin et al. |
| 2014/0256260 | A1 | 9/2014 | Ueda et al. |
| 2014/0342670 | A1 | 11/2014 | Kang |
| 2015/0119077 | A1* | 4/2015 | Buchheim ................ G01S 5/14 455/456.1 |
| 2015/0154557 | A1 | 6/2015 | Skaaksrud |
| 2015/0269549 | A1* | 9/2015 | Herring ............... G06Q 20/203 705/18 |
| 2016/0065005 | A1 | 3/2016 | Won |
| 2016/0099758 | A1* | 4/2016 | Bell ..................... H02J 50/001 307/104 |
| 2016/0100276 | A1* | 4/2016 | Viswanadham ...... H04W 8/005 455/41.2 |
| 2016/0132758 | A1 | 6/2016 | Connolly |
| 2017/0013547 | A1 | 1/2017 | Skaaksrud |
| 2017/0026723 | A1 | 1/2017 | Wan |
| 2017/0026905 | A1 | 1/2017 | Denboer et al. |
| 2017/0176582 | A1 | 6/2017 | Bjorkengren |
| 2017/0216611 | A1 | 8/2017 | Yoder |
| 2017/0279164 | A1* | 9/2017 | Herrema ............... H01M 10/06 |
| 2017/0359798 | A1* | 12/2017 | Bradley ............. H04M 1/6066 |
| 2018/0000563 | A1 | 1/2018 | Shanjani |
| 2018/0007523 | A1* | 1/2018 | Knaappila ............... H04W 4/21 |
| 2018/0012471 | A1 | 1/2018 | Bauer |
| 2018/0101704 | A1* | 4/2018 | Ng ........................ G06Q 10/00 |
| 2018/0103414 | A1 | 4/2018 | Golsch |
| 2018/0159618 | A1* | 6/2018 | Winata ................... H04W 4/80 |
| 2018/0191205 | A1 | 7/2018 | Koeppel |
| 2018/0199342 | A1 | 7/2018 | Rai |
| 2018/0220384 | A1* | 8/2018 | Kerai ..................... H04W 4/80 |
| 2019/0132331 | A1 | 5/2019 | Pignorel |
| 2019/0327675 | A1* | 10/2019 | Takeuchi ............. H04W 76/40 |

OTHER PUBLICATIONS

Extended European Search Reported dated Dec. 10, 2020, which issued in corresponding European Patent Application No. 18774252.3.

* cited by examiner

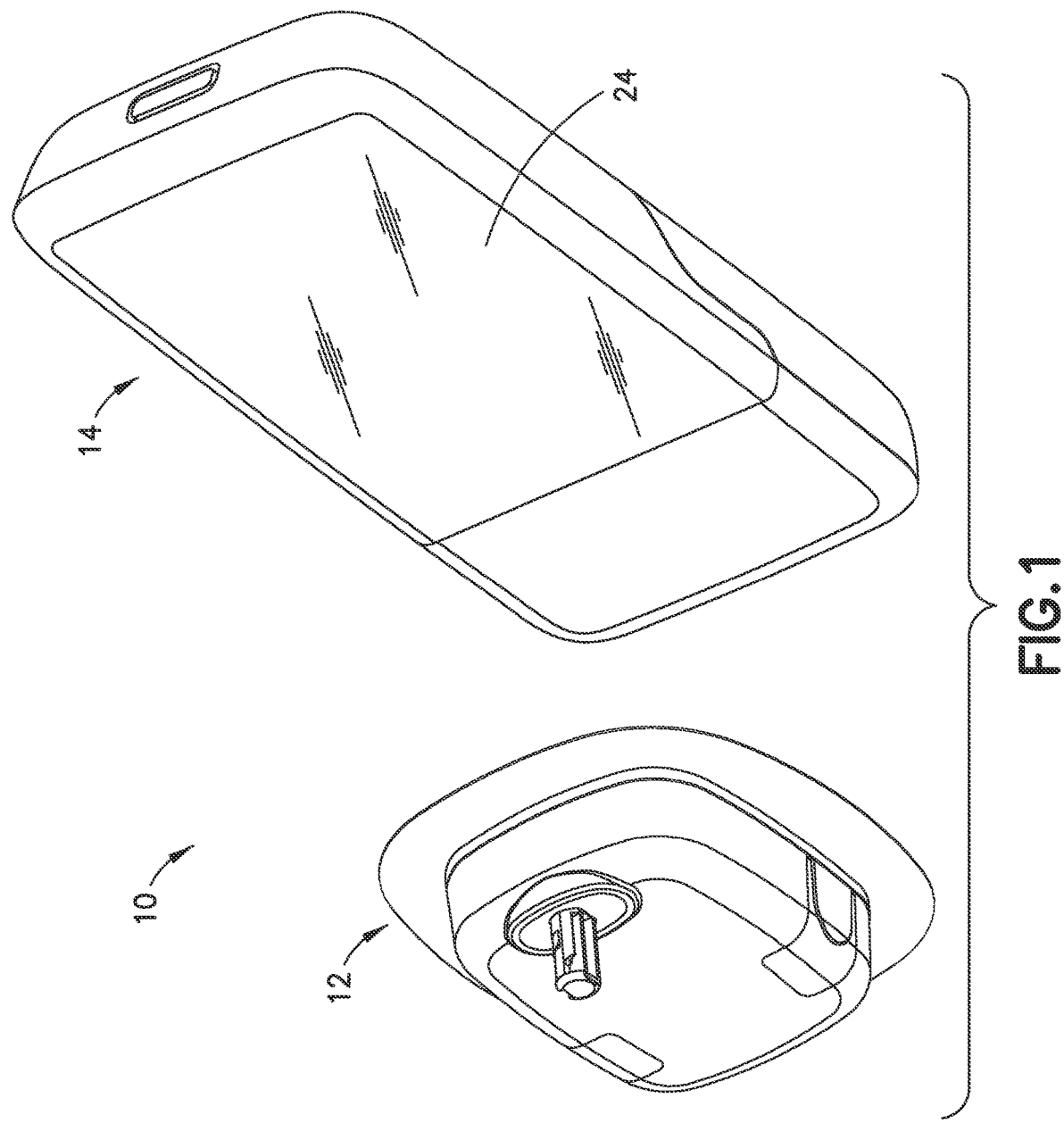

SYSTEMS, APPARATUSES AND METHODS FOR SECURE INDUCTIVE PAIRING BETWEEN TWO DEVICES

This application is a continuation of U.S. patent application Ser. No. 16/497,068, filed Sep. 24, 2019, which claims the benefit under 35 U.S.C. § 371 of PCT/US2018/023299, filed Mar. 20, 2018, which claims the benefit under 35 U.S.C. § 119(e) of U.S. provisional patent application Ser. No. 62/478,256, filed Mar. 29, 2017; the contents of each being incorporated herein by reference in its entirety.

BACKGROUND OF THE INVENTION

Field of the Invention

The present invention relates to systems, methods and apparatuses for secure inductive pairing between two devices, and particularly to minimizing pairing between a device and an unintended device.

Description of Related Art

Demand for on-body medical devices (e.g., wearable infusion pumps) and body area network (BAN) medical devices (e.g., handheld blood glucose meters, smart phones with diabetes management apps, and wireless controllers for on-body devices) has been increasing along with an increase in patients' and healthcare providers' desire for better and more convenient patient management of medical conditions such as diabetes.

Secure pairing between two devices, such as between a wearable medical device and a separate dedicated controller or smart phone with app related to the wearable medical device, is important to avoid unintended operations, or possibly malicious interference with the operations, of the medical device. Further, avoidance of pairing the medical device with another unintended device is also important, particularly when there are multiple potential devices with which a medical device can be paired within the same area.

A need exists for secure pairing of a medical device with an intended device, even when multiple devices are within the range of signals used for pairing operations.

SUMMARY OF THE INVENTION

The above and other problems are overcome, and additional advantages are realized, by illustrative embodiments of the present invention.

It is an aspect of illustrative embodiments of the present invention to provide a method of pairing a first device with a second device for wireless communication therebetween comprising: the first device transmitting inductive pulses via a near field communication (NFC) antenna, and scanning during scanning windows of selected duration via a first antenna having a different operational range than the NFC antenna; and a second device starting a timer upon detecting one of the inductive pulses from the first device via a near field communication (NFC) antenna, transmitting advertising signals at intervals via a second antenna having a similar operational range to the first antenna, and generating time stamps for each of its advertising signals using the timer and transmitting respective ones of the time stamps with corresponding ones of the advertising signals. The first device synchronizes the scanning windows with corresponding ones of the advertising signals using the time stamps.

In accordance with aspects of illustrative embodiments of the present invention, the selected duration of the scanning windows is selected to avoid detecting advertising signals from a third device during one of the scanning windows of the first device.

In accordance with aspects of illustrative embodiments of the present invention, the method further comprises: a third device transmitting inductive pulses via a near field communication (NFC) antenna, and scanning during scanning windows of selected duration via a third antenna having a similar operational range to the first antenna; and a fourth device starting a timer upon detecting one of the inductive pulses from the third device via a near field communication (NFC) antenna, transmitting advertising signals at intervals via a fourth antenna having a similar operational range to the first antenna, and generating time stamps for each of its advertising signals using the timer and transmitting respective ones of the time stamps with corresponding ones of the advertising signals. The third device synchronizes its scanning windows with corresponding ones of the advertising signals from the fourth device using its time stamps, the selected duration of the scanning windows of the third device being limited to avoid receiving the advertising signals of the second device during one of its scanning windows. The first device determines from the time stamps of the advertising signals received from the second device and the fourth device to pair with the second device and not the fourth device.

In accordance with aspects of illustrative embodiments of the present invention, the NFC antenna is a 13.56 Megahertz (MHz) antenna, and the first antenna having a different operational range than the NFC antenna operates in a radio frequency range of 2.40-2.48 Gigahertz (GHz).

In accordance with aspects of illustrative embodiments of the present invention, the method further comprises: the first device terminating scanning after detecting an advertising signal from the second device during one of the scanning windows of the first device; the first device transmitting a pairing command to the second device; and the second device sending a pairing response to the first device in response to receiving the pairing command.

In accordance with aspects of illustrative embodiments of the present invention, the method further comprises: the first device terminating scanning after detecting an advertising signal from the second device during one of the scanning windows of the first device; the first device transmitting a pairing command to the second device; the first device resuming transmitting scanning windows synchronized with corresponding ones of the advertising signals of the second device when no pairing response is received from the second device in response to the pairing command; and the first device retransmitting a pairing command to the second device.

It is an aspect of illustrative embodiments of the present invention to provide a first device for pairing with another device for wireless communication therebetween, the first device comprising: a near field communication (NFC) antenna; a first antenna having a different operational range than the NFC antenna; and a processing device configured to transmit inductive pulses via the NFC antenna, scan during scanning windows of selected duration via the first antenna, receive advertising signals and corresponding time stamps from a second device via the first antenna, the corresponding time stamps being generated by the second device upon detecting one of the inductive pulses transmitted from the first device, and synchronize the scanning windows with corresponding ones of the advertising signals using the time stamps.

In accordance with aspects of illustrative embodiments of the present invention, the processor is configured to determine a difference between advertising signals received from the second device and advertising signals received from a third device using the corresponding time stamps transmitted with the respective advertising signals by the second device and the third device, the time stamps sent with the respective advertising signals indicating an elapsed time between when the second device and the third device each detected one of the inductive pulses and commenced sending its advertising signals, and to transmit a pairing command to whichever of the second device and the third device is indicated as having advertising signals most synchronized with the scanning windows of the first device based on the time stamps.

In accordance with aspects of illustrative embodiments of the present invention, the processor is configured to terminate scanning when a pairing command is transmitted, and to resume scanning windows synchronized with corresponding ones of the advertising signals of the second device when no pairing response is received from the second device in response to the pairing command within a selected time period.

In accordance with aspects of illustrative embodiments of the present invention, the processor is configured to retransmit a pairing command to the second device after detecting an advertising signal from the second device during one of the scanning windows.

In accordance with aspects of illustrative embodiments of the present invention, the selected duration of the scanning windows is minimized to avoid detecting advertising signals from a third device during one of the scanning windows of the first device.

In accordance with aspects of illustrative embodiments of the present invention, the NFC antenna is a 13.56 Megahertz (MHz) antenna, and the first antenna operates in a radio frequency range at or greater than 2.40 Gigahertz (GHz).

Additional and/or other aspects and advantages of the present invention will be set forth in the description that follows, or will be apparent from the description, or may be learned by practice of the invention. The present invention may comprise devices to be paired and methods for operating same having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The above and/or other aspects and advantages of embodiments of the invention will be more readily appreciated from the following detailed description, taken in conjunction with the accompanying drawings, of which:

FIG. 1 depicts a medical device and a controller in accordance with an illustrative embodiment of the present invention;

Throughout the drawing figures, like reference numbers will be understood to refer to like elements, features and structures.

DETAILED DESCRIPTION OF ILLUSTRATIVE EMBODIMENTS

Figure 2A:
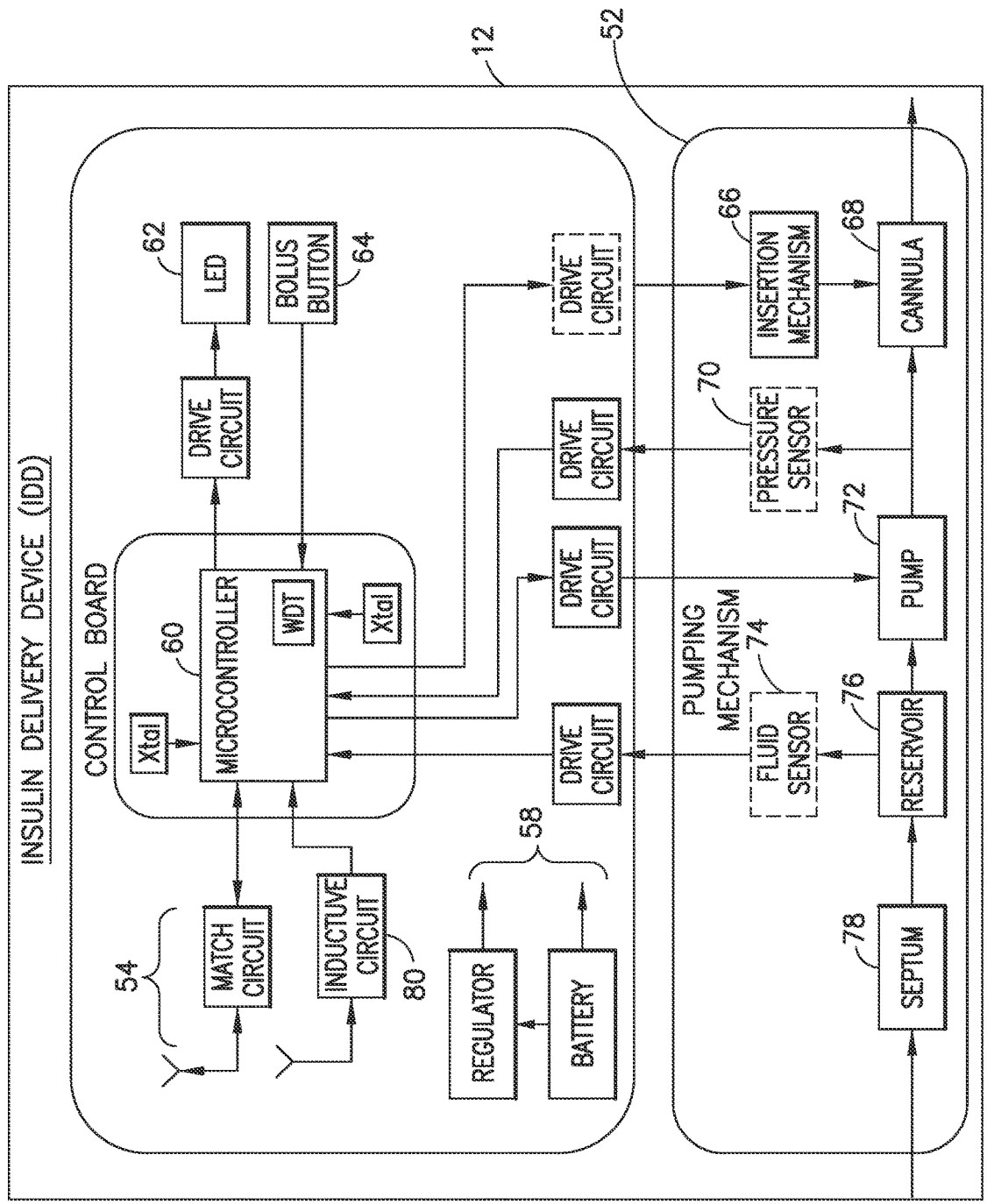
FIGS. 2A and 2B are block diagrams of the medical device and the controller in accordance with an illustrative embodiment of the present invention.

Reference will now be made in detail to embodiments of the present invention, which are illustrated in the accompanying drawings. The embodiments described herein exemplify, but do not limit, the present invention by referring to the drawings.

Figure 2B:
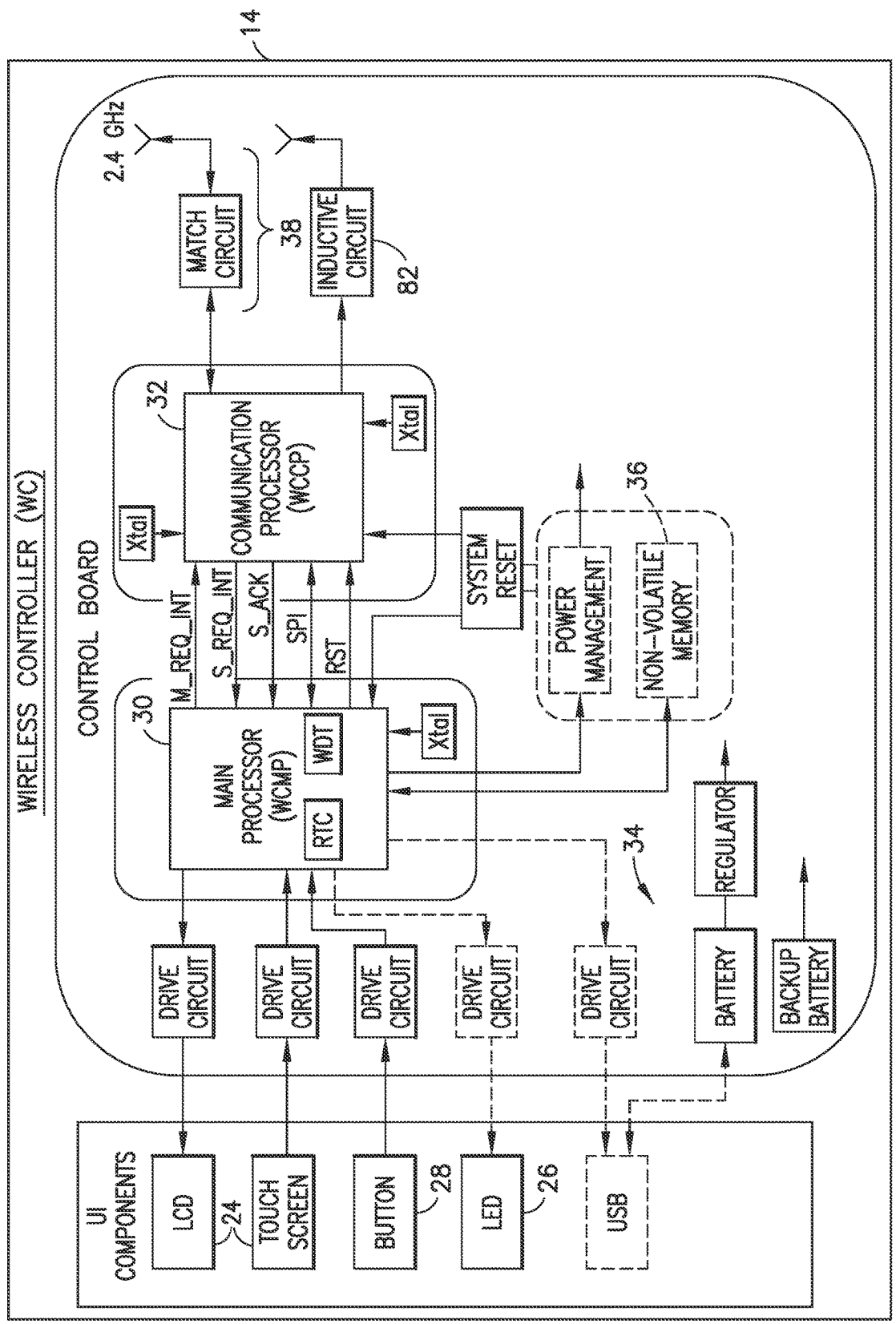

With reference to FIGS. 1, 2A and 2B, an illustrative medication delivery system 10 is shown having a medical device 12 and a controller 14 with display 24 or other user interface.

The medical device 12 can be a wearable device or a patient-carried device. The medical device 12 can have an integrated user interface as its controller 14, or the medical device can be configured to be controlled by a separate controller device such as a wireless controller 14 as shown in FIG. 1. In the illustrated embodiment, the medical device 12 is controlled by a wireless controller 14, but it is to be understood that aspects of the present invention apply to a medical device 12 with its own controller and another device 14 to be paired with the medical device 12.

For example, the medical device 12 can be a disposable insulin delivery device (IDD) for single patient use that is configured for continuous subcutaneous delivery of insulin at set and variable basal (24-hour period) rates and bolus (on-demand) doses for the management of patients with Type 2 Diabetes Mellitus (T2DM) requiring insulin therapy. It is to be understood, however, that the medical device 12 can be any on-body medical device (e.g., wearable infusion pump, continuous glucose meter) or body area network (BAN) medical device (e.g., handheld blood glucose meter, smart phone with medical condition management apps, or wireless controller for on-body device).

The IDD 12 is part of a system 10 that is an advanced insulin delivery system for use by patients with Type 2 Diabetes Mellitus (T2DM). It is configured for 24-hour-a-day use in all environments typically inhabited by the target users. It is configured for the patient user to wear the IDD for a period of three days (up to 84 hours). It has four (4) main functions: delivering user-set daily basal insulin rate; delivering user-set bolus insulin amount; delivering manual bolus insulin dose(s); and generating system status and notifications. The system addresses an unmet need for many Type 2 patients on multiple daily injections (MDI) requiring discreet, simple and cost effective insulin delivery alternative to the traditional complex insulin pump. It is to be understood, however, that the medical device 12 can be used to deliver any type of fluid and is not limited to insulin delivery, or delivery to only Type 2 patients.

The Wireless Controller (WC) 14 is used to program the body-worn IDD to deliver a daily basal insulin rate and meal-time insulin amount to the patient. The WC 14 also provides status information of the IDD 12 as well as notifications to the user. The body-worn IDD 12 stores and administers insulin to the patient subcutaneously. The IDD sends feedback to the patient via the WC if it detects issues (e.g., low volume in the reservoir, low battery). An important function supported by communication software in the system 10 is the wireless communication between the WC 14 and IDD 12, which enables the IDD 12 to provide the feedback to the WC 14 and for the user to control their insulin delivery by the IDD 12 wirelessly via the WC 14 in a simple and discrete way.

In the illustrated embodiment shown in FIG. 2A, the IDD 12 has a microcontroller 60 configured to control a pumping mechanism 52, wireless communication with the WC 14 (e.g., via an RF circuit 54 having a match circuit and antenna), and pump operations. The IDD has a bolus button(s) 64 for manual delivery of medication in addition to programmed delivery of medication. The pumping mechanism 52 comprises a reservoir 76 for storing a fluid medication (e.g., insulin) to be delivered via a cannula 68 to the patient wearing the IDD, and a pump 72 for controllably delivering designated amounts of medication from the reservoir through the cannula. The reservoir 76 can be filled via a septum 78 using a syringe. The IDD has a manual insertion mechanism 66 for inserting the cannula 68 into a patient; however, the processor 60 can be configured to operate an optional drive circuit to automate operation of the insertion mechanism 66 to deploy the cannula 68 into the patient. Further, the IDD 12 can be optionally provided with a fluid sensor 74 or a pressure sensor 70. An LED 62 can be operated by the microcontroller 60 to be on or flash during one or more pump operations such as during reservoir priming, for example. The IDD 12 is powered by a battery and regulator as indicated at 58. When initializing the IDD 12 (e.g., powering on to begin pairing with the WC 14), the bolus button(s) 64 can be configured as wake-up button(s) that, when activated by the user, causes the IDD 12 to wake from a power conserving shelf mode.

In the illustrated embodiment shown in FIG. 2B, the WC 14 is implemented as a dual microprocessor component having: 1) a WC Main Processor (WCMP) 30, and a WC Communications Processor (WCCP) 32. The WCMP 30 is connected to the user interface (UI) components such as the LCD display with touch screen 24, one or more buttons 28, LED indicator 26, and the like. The WCCP 32 is connected to radio frequency (RF) components 38 (e.g., an antenna and a match circuit) and is mainly responsible for the WC 14's wireless communication with the IDD 12. The two processors 30, 32 communicate with each other through a serial peripheral interface (SPI). The two processors 30, 32 can also interrupt each other through two interrupt pins, M_REQ_INT and S_REQ_INT. It is to be understood that the WC 14 can also be configured as a single processor device.

With continued reference to FIG. 2B, the WC 14 is designed to be non-field serviceable (i.e. no parts to be inspected, adjusted, replaced or maintained by the user), except for replaceable alkaline batteries 34 for power. A non-volatile memory (e.g., FLASH memory) 36 is provided in the WC to store delivery and status data received from the IDD 12 such as delivery dates and times and amounts.

The LCD with capacitive touch screen 24 serves as the visual interface for the user by rendering visual and graphical outputs to the user (e.g., system information, instructions, visual notices, user configurations, data outputs, etc.), and by providing a visual interface for the user to enter inputs (e.g., device operation inputs such as IDD pairing and set up and dosing, and configuration parameters, and so on). The WC display with capacitive touch screen 24 detects (at least) single-touch gestures over its display area. For example, the touch screen is configured for recognizing user tactile inputs (tap, swipe, and button press), allowing for navigation within UI screens and applications. The touch screen 24 aids in executing specific system functionalities (i.e. IDD 12 setup and pairing with the WC 14, insulin dosing, providing user with dosing history, and IDD deactivation and replacement with another IDD, and so on) through specific user interactions. The WC 14 can also include a button 28 such as a device wake-up button that, when activated by the user, causes the WC 14 to wake from a power conserving sleep mode. The WC 14 can also have an LED 26 to indicate low battery status (e.g., indicate low battery state when there is 12 hours or less of usage remaining).

The WC 14 radio frequency (RF) interface with the IDD 12 is, for example, based on a Bluetooth® Low Energy or BLE-based communication protocol, although other wireless communication protocols can be used. In the medication delivery system 10, the WC 14 and IDD 12 communicate wirelessly within a distance of up to 10 feet or approximately 3 meters, utilizing the ISM band from 2400 MHz to 2480 MHZ spectrum. The WC 14 communicates with the IDD 12 while the IDD is adhered to the body in open air. The WC 14 is the central device or master, and the IDD 12 is the peripheral device or slave. Whenever the WCMP 30 wants to send information to the IDD 12 or retrieve information from the IDD 12, it does so by interacting with the WCCP 32, which in turn, communicates with the IDD 12 across the BLE link via the respective RF circuits 38 and 54.

With continued reference to FIGS. 2A and 2B, additional inductive RF circuits 80, 82 are provided to the IDD 12 and WC 14, respectively. As stated above, the two devices 12 and 14 communicate with each other through the Bluetooth Low Energy (BLE) wireless interface. The Bluetooth Low Energy protocol operates at a 2.4 GHz frequency band. Before the pairing, the devices 12 and 14 can communicate to any other BLE device in the range. Given the physics of antennas at 2.4 GHz, each of these devices 12 and 14 has a large RF communication range. This is typically several feet at reduced transmit power, and at times more than 100 feet. Thus, it is possible that there are multiple other BLE devices that are in range of the devices 12 and 14 during their pairing mode, which can lead to two wrong devices getting paired. To overcome this potential problem and in accordance with an illustrative embodiment of the present invention, the IDD 12 and WC 14 are each provided with an inductive RF circuit with corresponding 13.56 MHz antenna as indicated at 80 and 82 in FIGS. 2A and 2B, respectively. Accordingly, only one IDD 12 is in sufficiently close proximity of the WC 14 to pair with it. This proximity range can be adjusted from fraction of an inch to few inches.

A number of advantages are realized by this illustrative embodiment of the present invention. For example, interference between WC and IDD is minimized because the antennas work only in a narrow range for 13.56 MHz and over a very short distance. In addition, an inductive pulse can be generated and used to synchronize the WC scanning window to the IDD advertisement. Finally, the present invention provides a low cost solution to the problem of unintended pairing between devices which can be a significant problem, particularly when one or both devices is a medical device and unintended pairing can be potentially injurious due to compromised operation of the medical device.

As described above in connection with FIG. 2B, the WC 14 has two microprocessors: a main microprocessor (WCMP) 30 and a communication microprocessor (WCCP) 32. On the WC 14, both antennas, that is, the inductive antenna 82 and the BLE antenna 38, are connected to the communication processor (WCCP) 32. On the IDD 12, the the inductive antenna 80 and the BLE antenna 54 are connected to the IDD processor 60. The inductive antennas

80, 82 are preferably only used for transmitting and receiving 13.56 MHz inductive pulses at the IDD 12 startup to synchronize the pairing process of the two devices 12 and 14. The BLE antennas 38, 54 are used for the data communications between the WC 14 and IDD 12 (e.g., during setup, daily use for delivering medication and IDD deactivation and replacement).

The inductive pairing is basically a process which uses inductive pulses to synchronize the BLE pairing between a WC 14 and an IDD 12. For the following description, it is understood that the IDD processor 60 is awake and no longer in a shelf mode or power conserving sleep mode at the time of inductive pairing (e.g., the IDD 12 can require a user to press the bolus button(s) 64 to wake up the device when first setting up the device from shelf mode).

Figure 3:
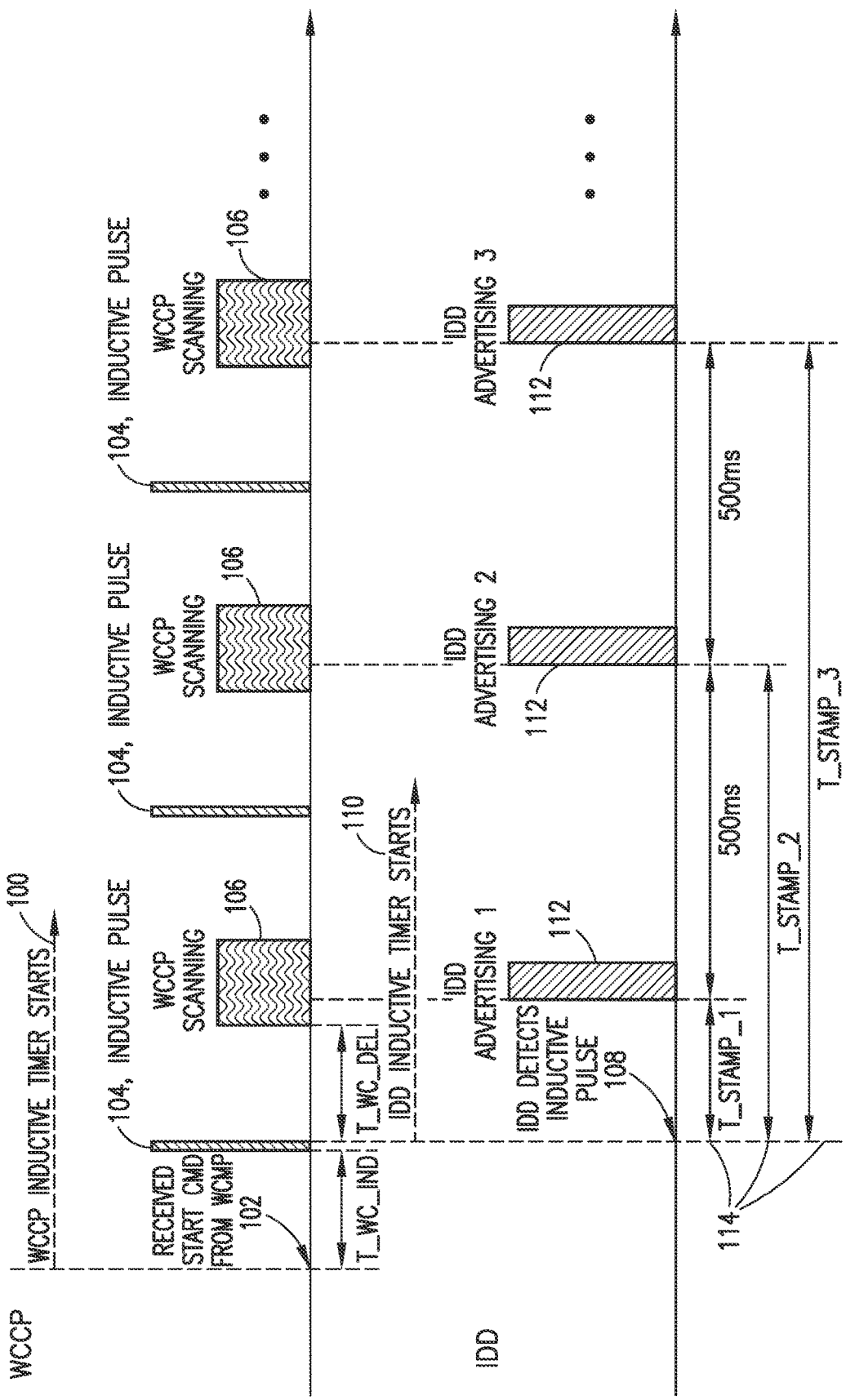
FIGS. 3, 4A and 4B, 5, 6, 7, 8, 9, 10 and 11 are diagrams of signals transmitted from the medical device and the controller in accordance with an embodiment of the present invention.

As shown in FIG. 3, at IDD 12 startup, after receiving the Start command 102 from the WCMP 30, the WCCP 32 will start a timer 100 and begin transmitting 13.56 MHz inductive pulses 104 (e.g., every 500 ms). Upon detecting one of the inductive pulses 104 with its antenna 80, the IDD 12 will start an inductive timer 110 and send Startup Advertisements 112 (e.g., every 500 ms) with the corresponding timestamp 114. Once the IDD 12 commences advertising (e.g., sending advertising signals 112 very 500 ms), the WCCP 32 synchronizes scanning windows 106 around the IDD 12's advertising events 112.

Figures 4, 4A, 4B:
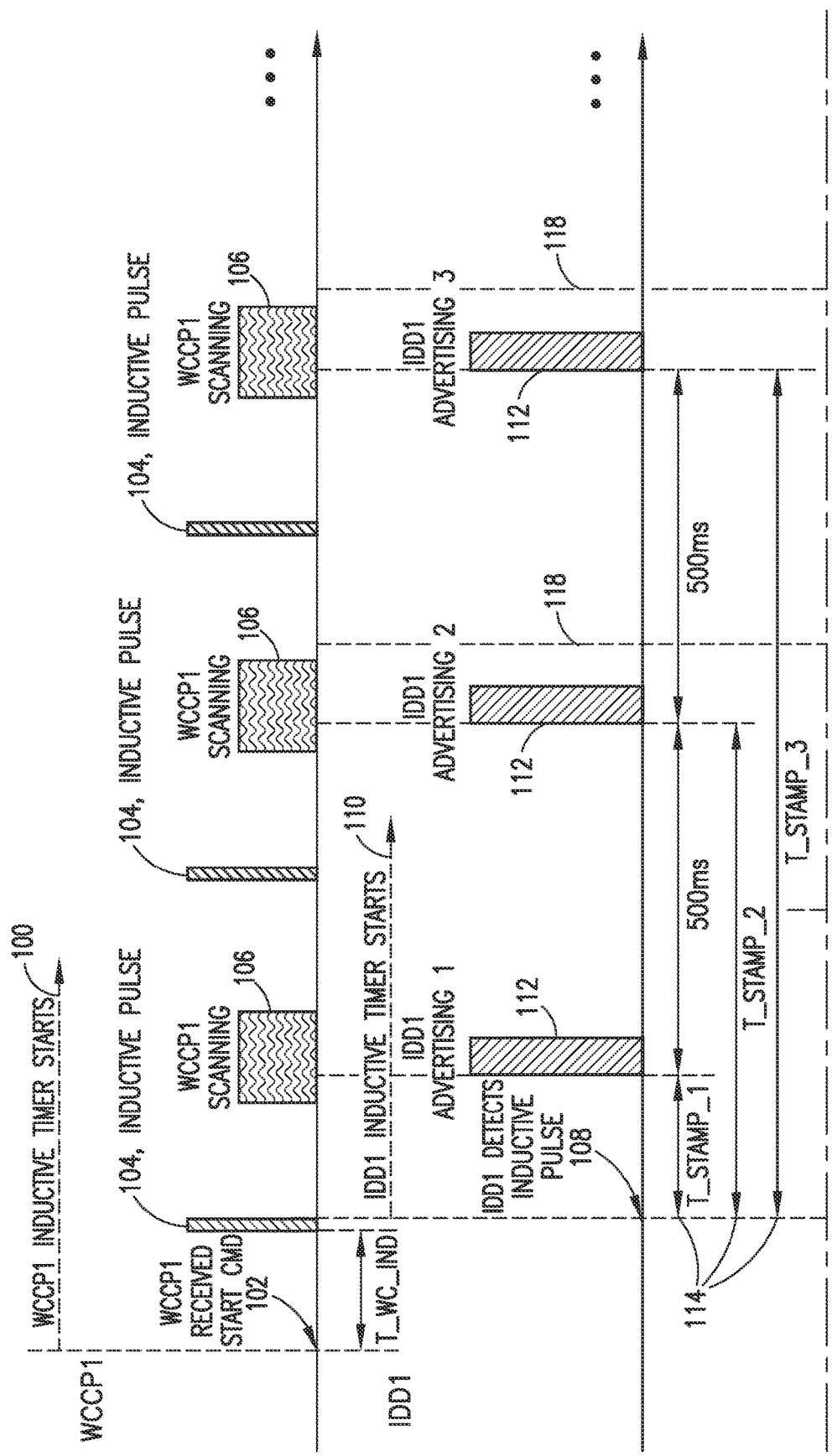
Figure 4B:
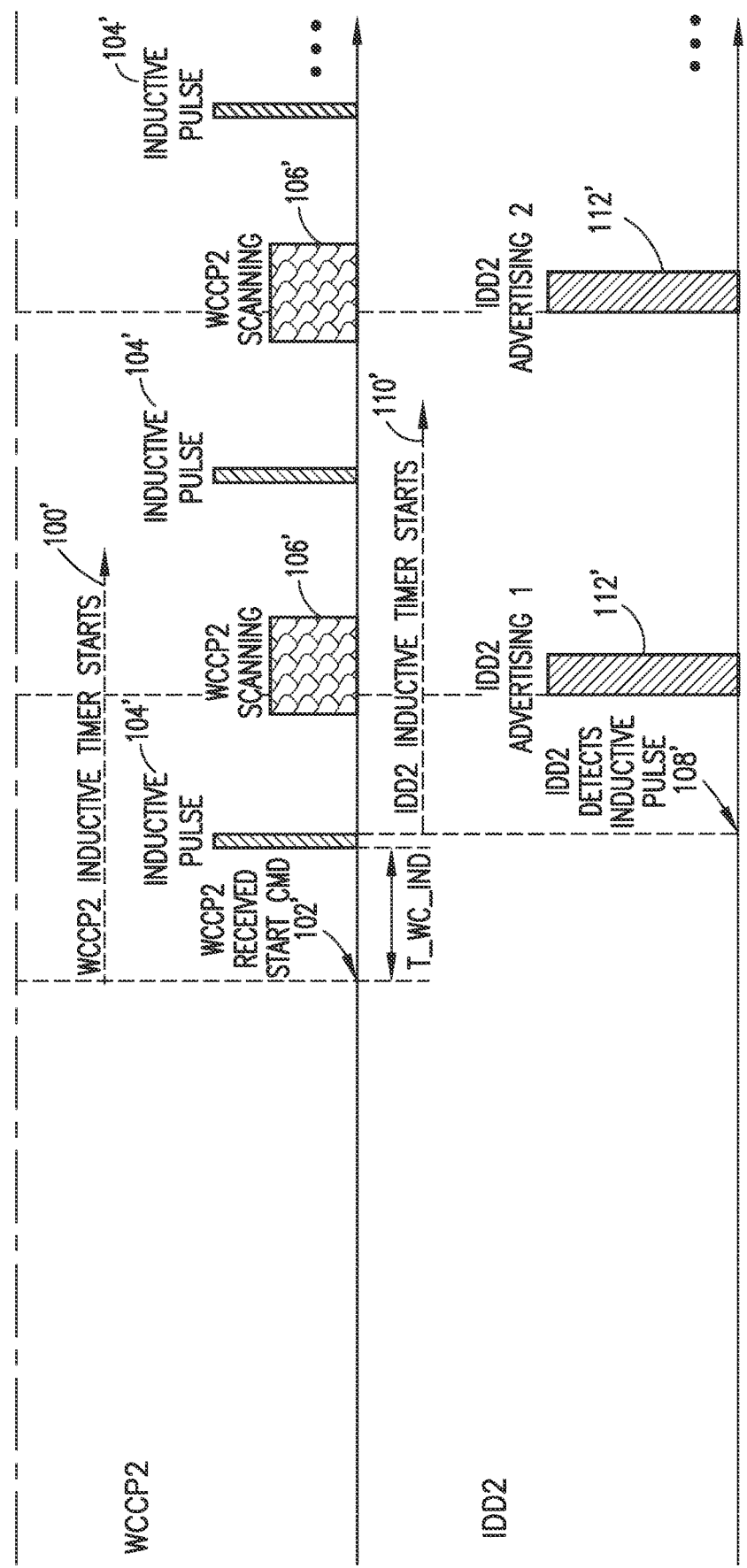

The scanning window 106 can be made very small to ensure that only one device (e.g., one IDD 12 among several devices around the WC 14) is seeking pairing with the WC 14 within and only within that time window 106, as illustrated at 118 in FIGS. 4A and 4B. For example, the scanning windows 106' of a second set of devices (e.g., WCCP2 32' and IDD2 12') are timed such that they will detect the advertising data 112' of the IDD2 12' but not the advertising data packet 112 of the IDD1 12 and vice versa. The time stamps 114 sent with the respective advertising signals 112 indicates the elapsed time between when the IDD detects the inductive pulse and the IDD sends the advertisement, which is used for distinguishing between the advertising signals 112 of the IDD 12 from those 112' that may be present from an unintended IDD2 12'.

Figure 5:
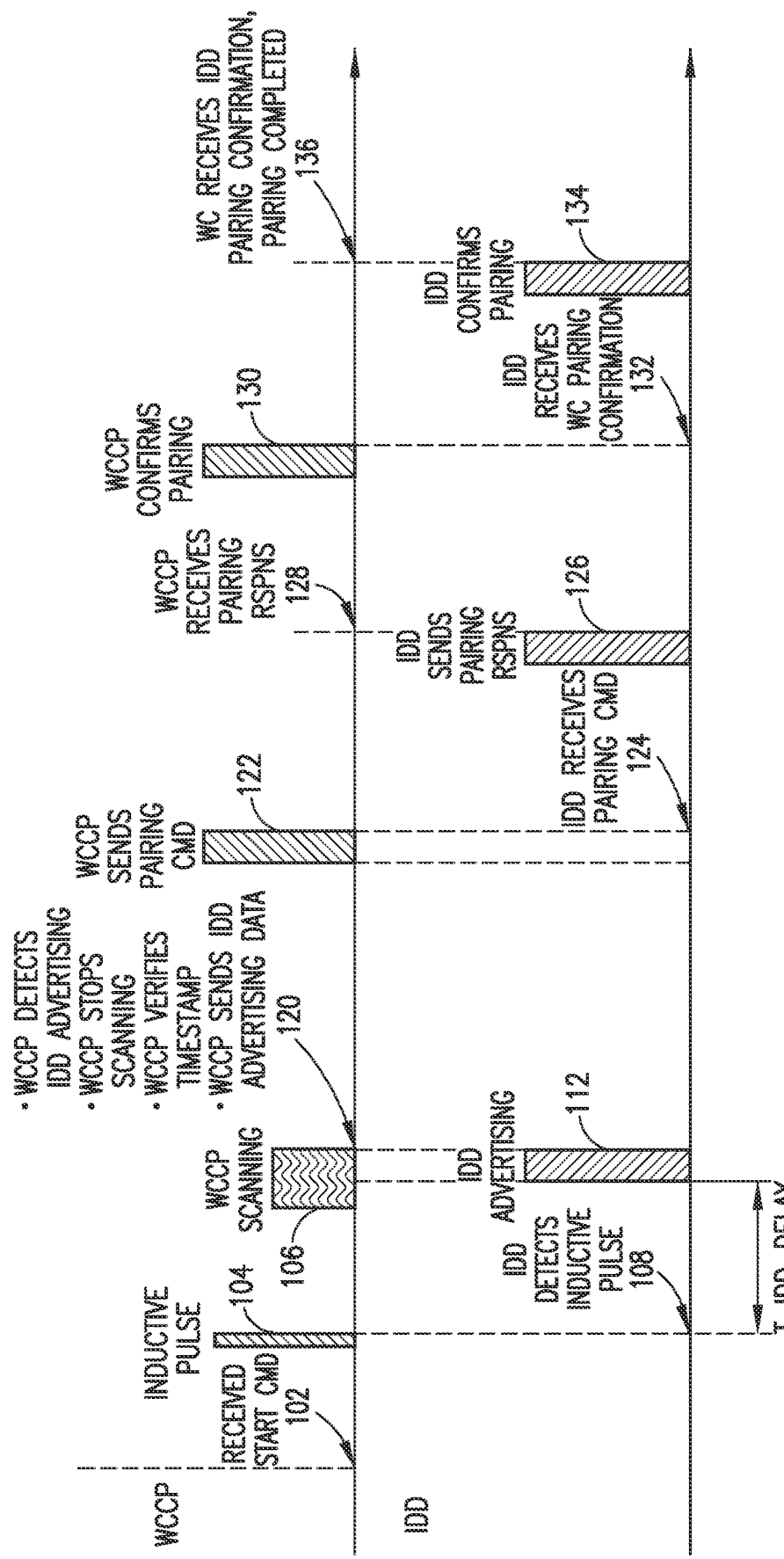

FIG. 5 illustrates successful pairing whereby the WCCP 32 receives a Start command 102 and commences sending inductive pulses 104. The IDD 12 detects the pulse at 108 and commences sending Advertisements 112. As shown in FIG. 5, the WCCP 32 detects the Advertisement 112 during its scanning window 106 and stops scanning, as indicated at 120. The WCCP 32 verifies the time stamp of the detected Advertisement 112 and sends IDD advertising data to the WCMP. The WCCP 32 sends a pairing command 122. The IDD receives the pairing command 124 and sends a pairing response 126. Once the WCCP 32 receives the pairing response 128, the WCCP 32 transmits a pairing confirmation 130. The IDD receives the WC pairing confirmation 132 and sends an IDD pairing confirmation 134. When the WC receives the IDD pairing confirmation 134, pairing is completer 126 as between the WC 14 and the IDD 12.

Figure 6:
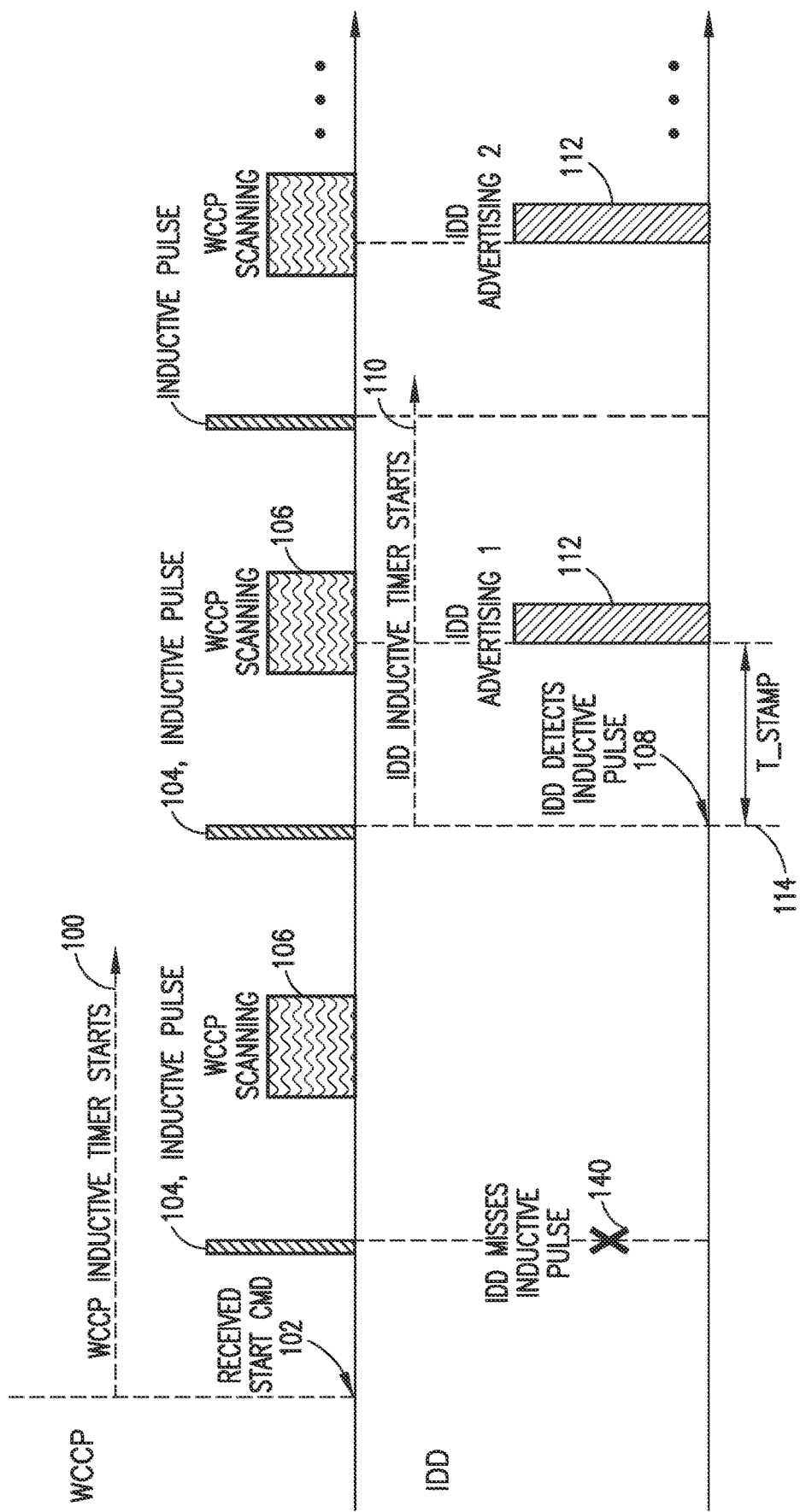
Figure 7:
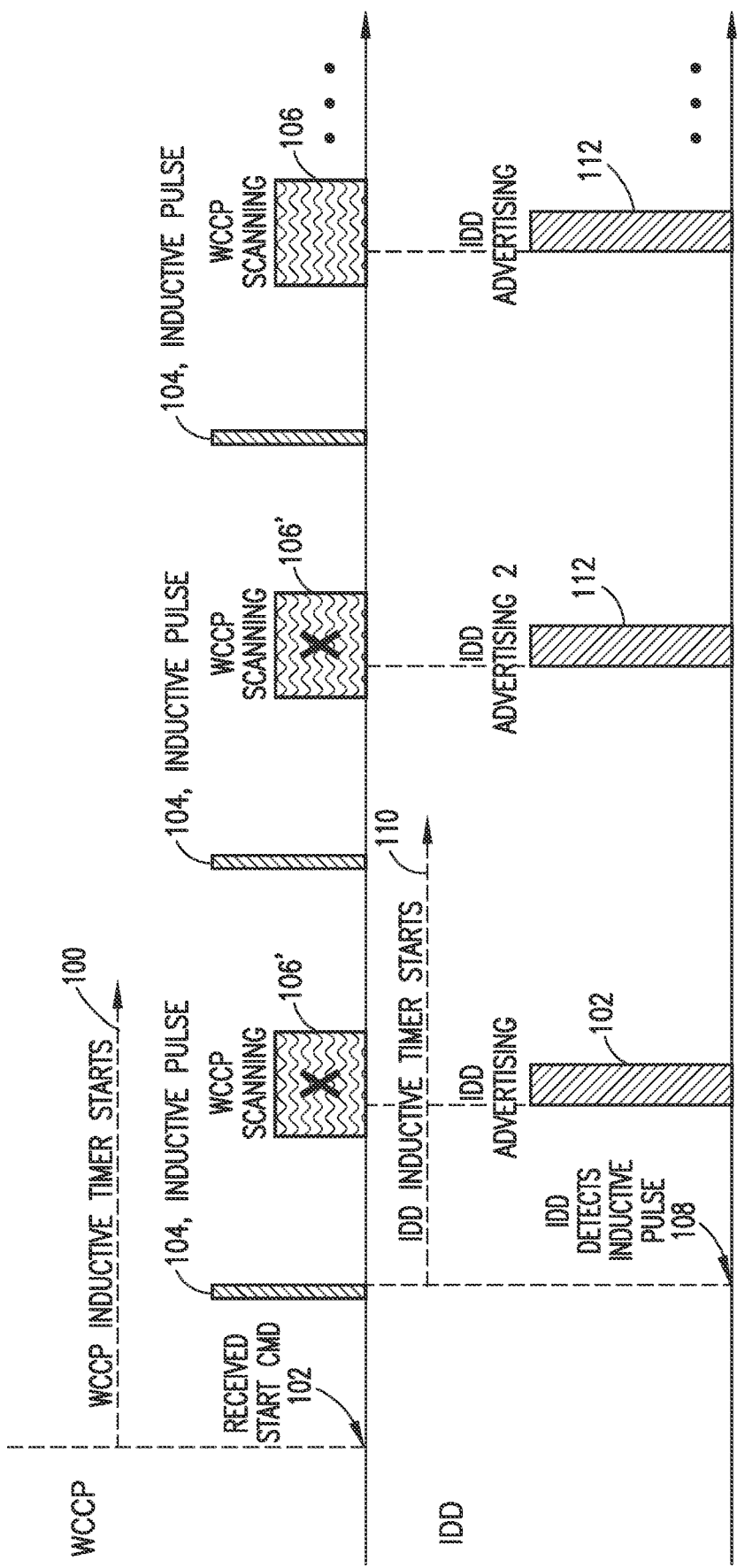

FIG. 6 illustrates an Error Condition 1 whereby the IDD 12 misses the inductive pulse 104 at the beginning, as indicated at 140, but is able to catch it later when the WCCP 32 retries transmitting inductive pulses 104. FIG. 7 illustrates an Error Condition 2 wherein the WCCP 32 does not detect the IDD advertisement 108 at the beginning as indicated by the two scanning windows 106', but is able to catch the IDD advertisement 112 later, as indicated by 106 in FIG. 7, after the IDD 12 retries.

Figure 8:
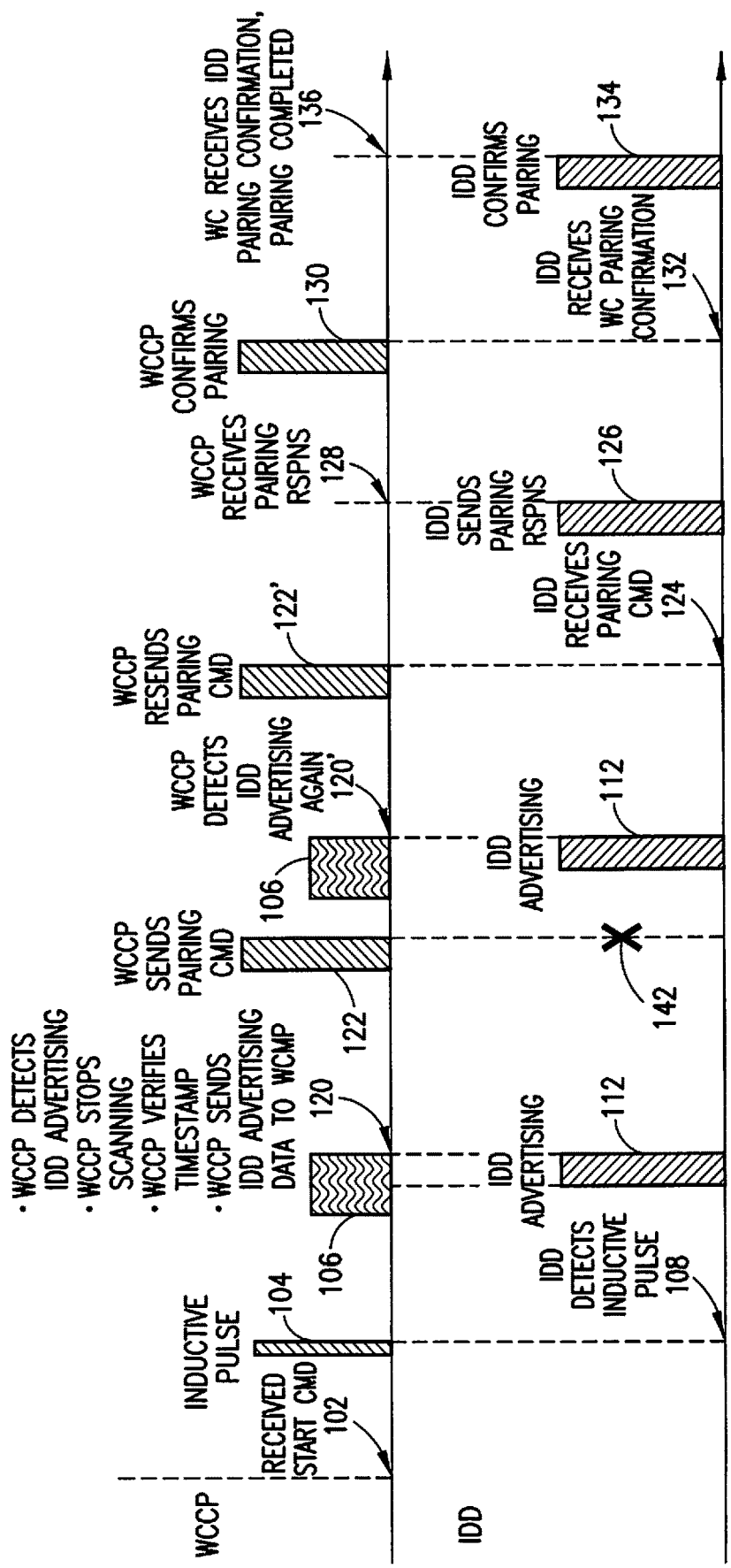
Figure 9:
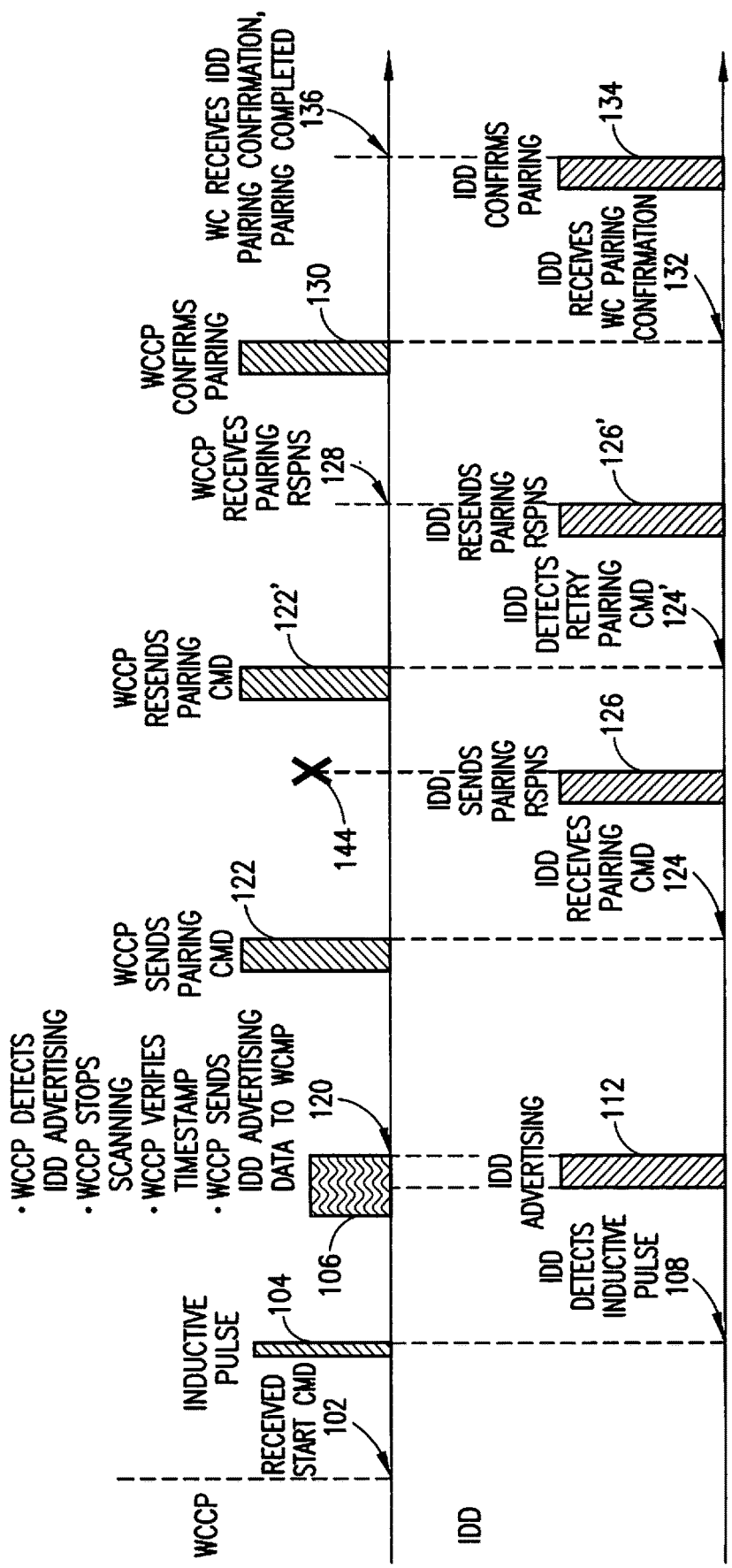

FIG. 8 illustrates an Error Condition 3 whereby the IDD 12 misses the pairing command 122 at first, as indicated at 142, but is able to receive the pairing command 124 later after the WCCP 32 retries sending it as indicated at 122'. FIG. 9 illustrates an Error Condition 4 whereby the WCCP 32 misses the IDD pairing response 126 at first, as indicated at 144, but is able to recover by resending the pairing command 122' and receiving the IDD pairing response 126' as indicated at 128.

Figure 10:
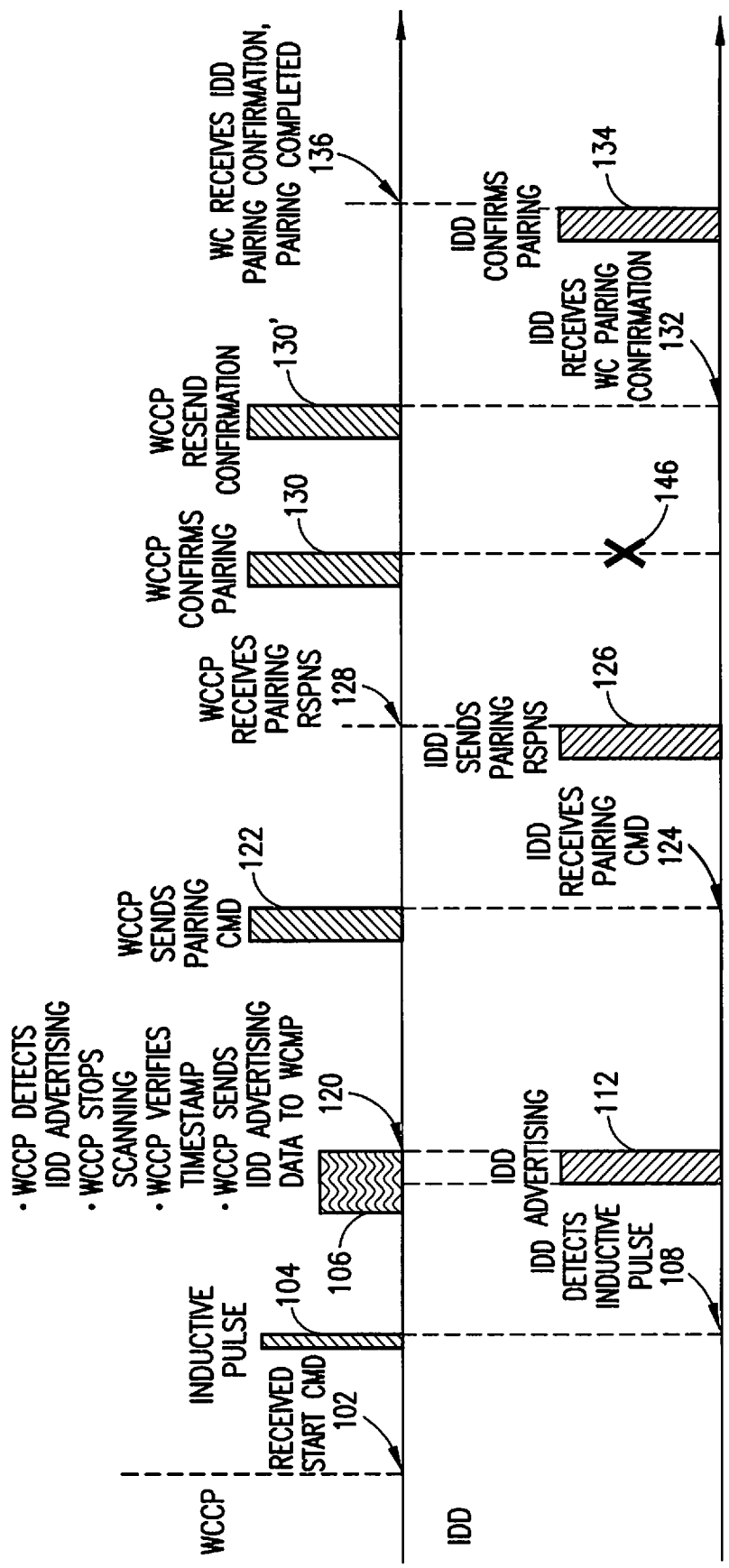
Figure 11:
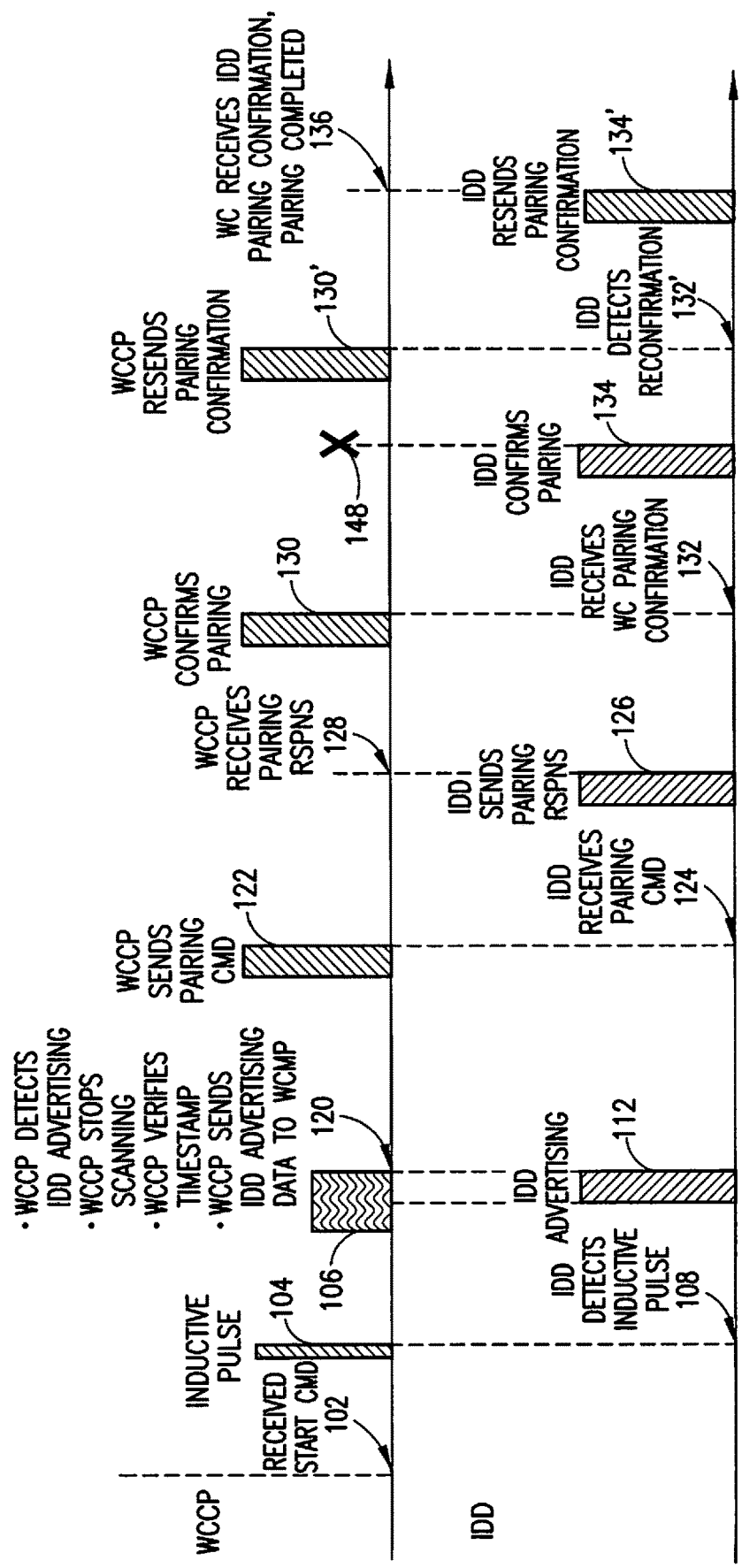

FIG. 10 illustrates an Error Condition 5 whereby the IDD 12 misses the WCCP pairing confirmation 130 at first, as indicated at 146, but is able to recover it as indicated at 132 when the WCCP 32 resends the pairing confirmation 130'. FIG. 11 illustrates an Error Condition 6, whereby the WCCP 32 misses IDD pairing confirmation 132 at first, but is able to recover it as indicated at 130' when the IDD 12 resends the IDD pairing confirmation 134'.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The components of the illustrative devices, systems and methods employed in accordance with the illustrated embodiments of the present invention can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Also, functional programs, codes, and code segments for accomplishing the present invention can be easily construed as within the scope of the invention by programmers skilled in the art to which the present invention pertains. Method steps associated with the illustrative embodiments of the present invention can be performed by one or more programmable processors executing a computer program, code or instructions to perform functions (e.g., by operating on input data and/or generating an output). Method steps can also be performed by, and apparatus of the invention can be implemented as, special purpose logic circuitry, e.g., an FPGA (field programmable gate array) or an ASIC (application-specific integrated circuit).

The various illustrative logical blocks, modules, and circuits described in connection with the embodiments disclosed herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in the remote station, Electronic medical device, a server, or a combination thereof. In the alternative, the processor and the storage medium may reside as discrete components in a user terminal.

The above-presented description and figures are intended by way of example only and are not intended to limit the present invention in any way except as set forth in the following claims. It is particularly noted that persons skilled in the art can readily combine the various technical aspects of the various elements of the various illustrative embodiments that have been described above in numerous other ways, all of which are considered to be within the scope of the invention.

The invention claimed is:

1. A first device for pairing with another device for wireless communication therebetween, the first device comprising:
a near field communication (NFC) antenna;
a first antenna having a different operational range than the NFC antenna; and
a processing device configured to transmit inductive pulses via the NFC antenna, scan during scanning windows of selected duration via the first antenna, receive advertising signals and corresponding time stamps from a second device via the first antenna, the corresponding time stamps being generated by the second device upon detecting one of the inductive pulses transmitted from the first device, and synchronize the scanning windows with corresponding ones of the advertising signals using the time stamps.

2. The first device of claim 1, wherein the processor is configured to determine a difference between advertising signals received from the second device and advertising signals received from a third device using the corresponding time stamps transmitted with the respective advertising signals by the second device and the third device, the time stamps sent with the respective advertising signals indicating an elapsed time between when the second device and the third device each detected one of the inductive pulses and commenced sending its advertising signals, and to transmit a pairing command to whichever of the second device and the third device is indicated as having advertising signals most synchronized with the scanning windows of the first device based on the time stamps.

3. The first device of claim 2, wherein the processor is configured to terminate scanning when a pairing command is transmitted, and to resume scanning windows synchronized with corresponding ones of the advertising signals of the second device when no pairing response is received from the second device in response to the pairing command within a selected time period.

4. The first device of claim 3, wherein the processor is configured to retransmit a pairing command to the second device after detecting an advertising signal from the second device during one of the scanning windows.

5. The first device of claim 1, wherein the selected duration of the scanning windows is minimized to avoid detecting advertising signals from a third device during one of the scanning windows of the first device.

6. The first device of claim 1, wherein the NFC antenna is a 13.56 Megahertz (MHz) antenna, and the first antenna operates in a radio frequency range at or greater than 2.40 Gigahertz (GHz).

* * * * *